United States Patent
DeVries et al.

[11] Patent Number: 6,090,942
[45] Date of Patent: Jul. 18, 2000

[54] PROCESS AND INTERMEDIATES FOR A $\beta_3$-ADRENERGIC RECEPTOR AGONIST

[75] Inventors: Keith M. DeVries, Chester; Jeffrey W. Raggon, Uncasville; Ravi M. Shanker, Groton; Frank J. Urban, Waterford; Brian C. Vanderplas, Old Lyme, all of Conn.

[73] Assignee: Pfizer Inc., New York, N.Y.

[21] Appl. No.: 09/408,998

[22] Filed: Sep. 29, 1999

Related U.S. Application Data

[60] Provisional application No. 60/104,375, Oct. 15, 1998, and provisional application No. 60/145,460, Jul. 23, 1999.

[51] Int. Cl.⁷ .......................... C07F 7/02; C07D 405/12; C07D 403/12
[52] U.S. Cl. .................. 546/14; 546/282.7; 546/284.4
[58] Field of Search .................. 546/14, 282.7, 546/284.4

[56] References Cited

U.S. PATENT DOCUMENTS 5,714,506  2/1998  Fisher et al. ............................ 514/352

*Primary Examiner*—Alan L. Rotman
*Assistant Examiner*—Rita Desai
*Attorney, Agent, or Firm*—Peter C. Richardson; Gregg C. Benson; Robert T. Ronau

[57] ABSTRACT

The instant invention relates to intermediates of Formula II,

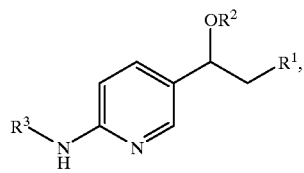

wherein $R^1$, $R^2$ and $R^3$ are as defined in the specification, and to processes for preparing such intermediates. This invention also relates to processes for preparing compounds of Formula III,

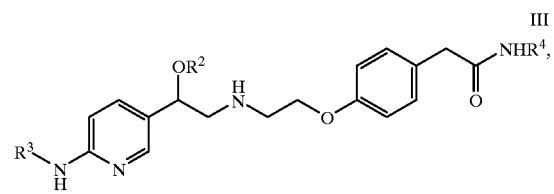

and enantiomers thereof, wherein $R^2$, $R^3$ and $R^4$ are as defined in the specification. Compounds of Formula II and Formula III are intermediates in the preparation of a potent $\beta_3$ adrenergic receptor agonist. The instant invention also relates to processes for preparing the $\beta_3$ adrenergic receptor agonist using the compounds of Formula II and Formula III.

10 Claims, No Drawings

PROCESS AND INTERMEDIATES FOR A β₃-ADRENERGIC RECEPTOR AGONIST

CROSS-REFERENCE

This application claims priority of provisional application No. 60/104,375 filed Oct. 15, 1998 and provisional application No. 60/145,460, filed Jul. 23, 1999.

BACKGROUND OF THE INVENTION

The present invention relates to certain compounds of Formula II below, which are useful intermediates in the synthesis of certain β₃-adrenergic receptor agonists having the general Formula I:

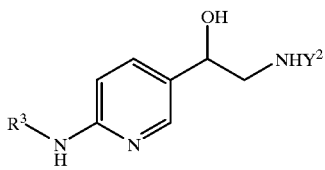

where $R^3$ is as defined below and $Y^2$ is

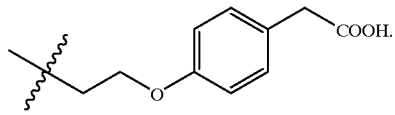

Examples of such substituents and the resultant β₃-adrenergic receptor agonists can be found in commonly assigned International Application Publication No. WO 94/35671. The invention also relates to processes for synthesizing the compounds of Formula II, which are useful intermediates in the synthesis of the compounds of Formula I. The invention further relates to processes for synthesizing the compounds of Formula I. The β₃-adrenergic receptor agonists also possess utility for increasing lean meat deposition and/or improving the lean meat to fat ratio in edible animals.

(4-(2-(2-(6-Aminopyridin-3-yl)-2(R)-hydroxyethyl-amino)ethoxy)phenyl)acetic acid has the structure of Formula XII:

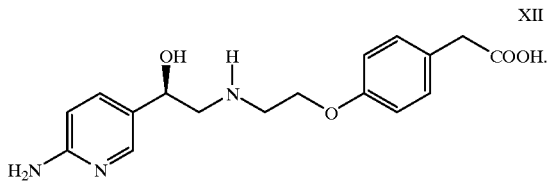

(4-(2-(2-(6-Aminopyridin-3-yl)-2(R)-hydroxyethyl-amino)ethoxy)phenyl)acetic acid is disclosed in commonly assigned International Patent Application Publication Number WO 96/35671, the disclosure of which is incorporated herein by reference, as a β-adrenergic agent. Accordingly, (4-(2-(2-(6-aminopyridin-3-yl)-2(R)-hydroxyethylamino)ethoxy)phenyl)acetic acid has utility in the treatment of obesity.

The β-adrenergic receptor agonists further possess utility in the treatment of intestinal motility disorders, depression, prostate disease, dyslipidemia, and airway inflammatory disorders such as asthma and obstructive lung disease.

The β₃-receptor is also expressed in human prostate. Because stimulation of the β₃-receptor causes relaxation of smooth muscles that have been shown to express the β₃-receptor (e.g. intestine), one skilled in the art would predict relaxation of prostate smooth muscle. Therefore, β₃-agonists will be useful for the treatment or prevention of prostate disease.

SUMMARY OF THE INVENTION

This invention is directed to compounds of Formula II,

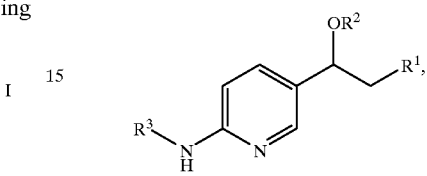

enantiomers thereof and pharmaceutically acceptable salts thereof, wherein:

$R^1$ is a leaving group selected from halo, methanesulfonyloxy, benzenesulfonyloxy, p-toluenesulfonyloxy, m-nitrobenzenesulfonyloxy and p-nitrobenzenesulfonyloxy;

$R^2$ is tetrahydrofuranyl, tetrahydropyranyl or a silyl protecting group; and $R^3$ is $(C_1$–$C_5)$alkanoyl or benzoyl optionally substituted with up to three $(C_1$–$C_4)$alkyl, $(C_1$–$C_4)$alkoxy or halo.

A preferred group of compounds, designated the A Group, comprises those compounds having the Formula II as shown above, enantiomers thereof and pharmaceutically acceptable salts thereof, wherein $R^2$ is $SiR^5R^6R^7$, wherein $R^5$, $R^6$ and $R^7$ are each independently $(C_1$–$C_4)$alkyl or aryl.

A preferred group of compounds within the A Group, designated the B Group, comprises those compounds, enantiomers thereof and pharmaceutically acceptable salts thereof wherein $R^3$ is acetyl, $R^1$ is toluenesulfonyloxy and said silyl protecting group is selected from t-butyldimethylsilyl, triethylsilyl and triisopropylsilyl.

A preferred group of compounds within the B Group, designated the C Group, comprises those compounds, enantiomers thereof and pharmaceutically acceptable salts thereof, wherein $R^2$ is t-butyldimethylsilyl.

A preferred compound within the C Group comprises the compound and pharmaceutically acceptable salts thereof having (R) stereochemistry.

A preferred compound of this invention is toluene-4-sulfonic acid 2-(6-acetylamino-pyridin-3-yl)-2(R)-(tert-butyldimethyl-silyloxy)-ethyl ester.

This invention is also directed to compounds of Formula III

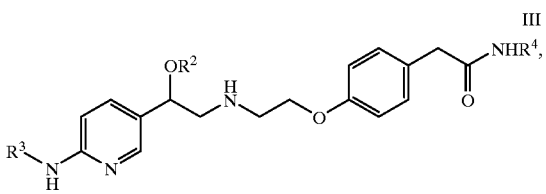

enantiomers thereof and pharmaceutically acceptable salts thereof, wherein:

$R^2$ is tetrahydrofuranyl, tetrahydropyranyl or a silyl protecting group;

R³ is (C₁–C₅)alkanoyl or benzoyl optionally substituted independently with up to three (C₁–C₄)alkyl, (C₁–C₄) alkoxy or halo; and R⁴ is (C₁–C₈)alkyl.

A preferred group of compounds, designated the D Group, comprises those compounds of Formula III, enantiomers thereof and pharmaceutically acceptable salts thereof, wherein said hydroxy protecting group is t-butyldimethylsilyl, triethylsilyl, trimethylsilyl, triisopropylsilyl or tetrahydropyranyl.

A preferred group of compounds within the D Group, designated the E Group, comprises those compounds, enantiomers thereof and pharmaceutically acceptable salts thereof, wherein R³ is acetyl, R² is t-butyldimethylsilyl, and R⁴ is methyl.

A preferred compound within the E Group comprises the compound and pharmaceutically acceptable salts thereof having (R) stereochemistry.

A preferred compound within this invention is 2-(4-(2-(2-(6-acetylamino-pyridin-3-yl)-2(R)-(t-butyldimethylsilyloxy)-ethylamino)-ethoxy)-phenyl-N-methyl-acetamide.

Another preferred compound within this invention is the monohydrochloride salt of (4-(2-(2-(6-aminopyridin-3-yl)-2(R)-hydroxyethylamino)ethoxy)phenyl)acetic acid.

This invention is also directed to a process, designated Process A, for preparing a compound of Formula II,

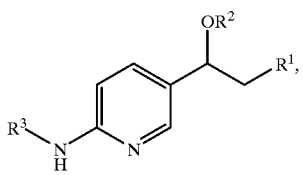

or enantiomers thereof, wherein

R¹ is a leaving group selected from halo, methanesulfonyloxy, p-toluenesulfonyloxy, benzenesulfonyloxy, m-nitrobenzenesulfonyloxy and p-nitrobenzenesulfonyloxy;

R² is tetrahydrofuranyl, tetrahydropyranyl or a silyl protecting group; and

R³ is (C₁–C₅)alkanoyl or benzoyl optionally substituted independently with up to three (C₁–C₄)alkyl, (C₁–C₄) alkoxy or halo, comprising reacting a compound of the Formula IV,

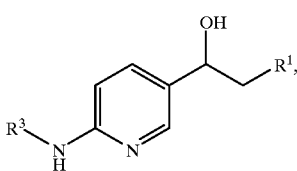

or enantiomers thereof, wherein R¹ and R³ are as defined above with a silylating agent and a suitable base in a reaction inert solvent for about 12 hours to about 18 hours at about 20° C. to about 50° C.

A preferred process within Process A, designated Process B, comprises the process wherein said suitable base is imidazole.

A preferred process within Process B, designated Process C, comprises the process wherein R¹ is p-toluenesulfonyloxy, R³ is acetyl and said silylating agent is t-butyldimethylchlorosilane.

A preferred process within Process C comprises the process wherein

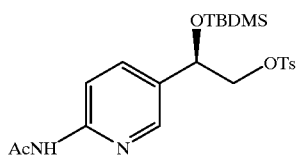

is prepared from

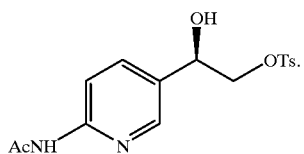

This invention is also directed to a process, designated Process D, for preparing a compound of the Formula III

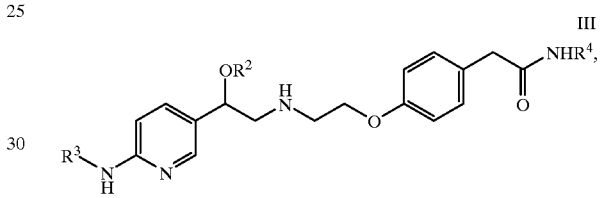

or enantiomers thereof, wherein R² is tetrahydrofuranyl, tetrahydropyranyl or a silyl protecting group; R³ is (C₁–C₅) alkanoyl or benzoyl optionally substituted independently with up to three (C₁–C₄)alkyl, (C₁–C₄)alkoxy or halo; and R⁴ is (C₁–C₈)alkyl comprising reacting a compound of the Formula II

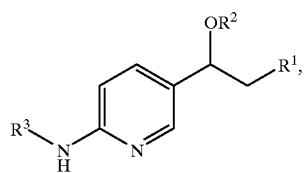

or enantiomers thereof, wherein R¹, R² and R³ are as defined above, with a compound of the Formula VII,

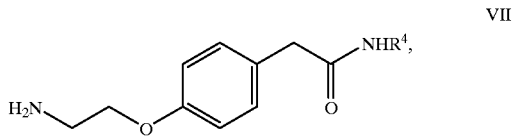

wherein R⁴ is (C₁–C₈)alkyl and a suitable base in a reaction inert solvent for a time of about 6 hours to 24 hours at a temperature of about 60° C. to 100° C.

A preferred process within Process D, designated Process E, is wherein said time is about 18 hours and said temperature is about 80° C. and which comprises the process wherein R² is t-butyldimethylsilyl, trimethylsilyl, triethylsilyl, triisopropylsilyl or tetrahydropyranyl and said suitable base is N,N-diisopropylethylamine, triethylamine, N-methylmorpholine or 1,4-diazabicyclo[2.2.2]octane.

A preferred process within Process E, designated Process F, comprises the process wherein $R^1$ is toluenesulfonyloxy, $R^2$ is t-butyldimethylsilyl; $R^3$ is acetyl; and $R^4$ is methyl.

A preferred process within Process F comprises the process wherein the compound of Formula VIII,

VIII

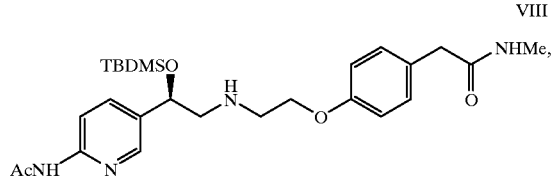

is prepared from the compound of Formula V,

V

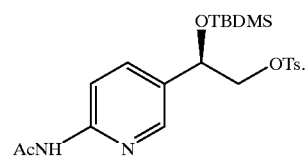

This invention is also directed to a process, designated Process G, for preparing a compound of Formula IX,

IX

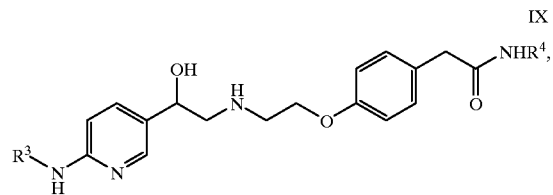

or enantiomers thereof, wherein $R^3$ is $(C_1-C_5)$alkanoyl or benzoyl optionally substituted independently with up to three $(C_1-C_4)$alkyl, $(C_1-C_4)$alkoxy or halo and $R^4$ is $(C_1-C_8)$alkyl comprising reacting a compound of Formula III

III

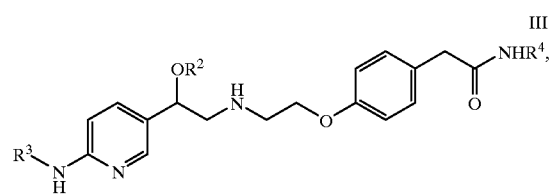

or enantiomers thereof, wherein $R^2$ is tetrahydrofuranyl, tetrahydropyranyl or a silyl protecting group and $R^3$ and $R^4$ are as defined above with a fluoride source in a reaction inert solvent for a time of about 6 hours to about 12 hours at a temperature of about 0° C. to about 50° C.

A preferred process within Process G, designated Process H, is wherein said temperature is about room temperature and which comprises the process wherein $R^2$ is t-butyldimethylsilyl and said fluoride source is tetrabutylammonium fluoride.

A preferred process within Process H, designated Process I, comprises the process wherein $R^3$ is acetyl and $R^4$ is methyl.

A preferred process within Process I, designated Process J, comprises the process wherein the compound of Formula X,

X

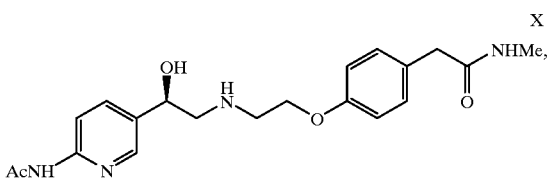

is prepared from the compound of Formula VIII,

VIII

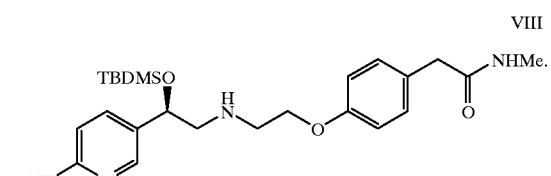

This invention is also directed to a process, designated Process K, for preparing a compound of Formula IX-a,

IX

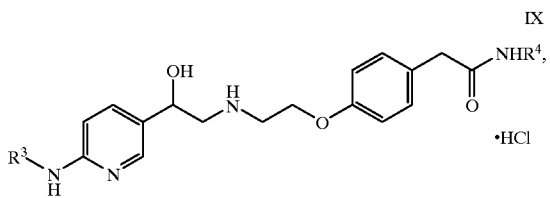

or enantiomers thereof, wherein $R^3$ is $(C_1-C_5)$alkanoyl or benzoyl optionally substituted independently with up to three $(C_1-C_4)$alkyl, $(C_1-C_4)$alkoxy or halo and $R^4$ is $(C_1-C_8)$alkyl comprising (a) reacting a compound of Formula III

III

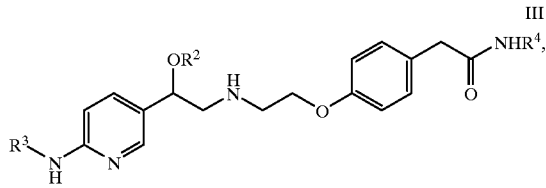

or an enantiomer thereof, wherein $R^2$ is tetrahydrofuranyl, tetrahydropyranyl or a silyl protecting group and $R^3$ and $R^4$ are as defined above with a fluoride source in a reaction inert solvent for about 6 hours to about 12 hours at a temperature of about 0° C. to about 50° C. to form a compound of Formula IX

IX

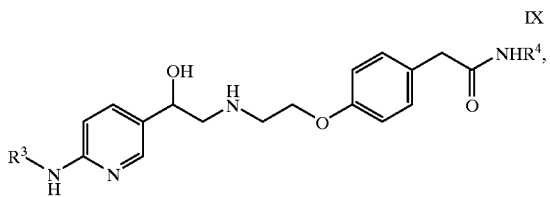

or an enantiomer thereof, wherein $R^3$ and $R^4$ are as defined above and (b) reacting said compound of Formula IX or an enantiomer thereof, with two equivalents of hydrochloric acid in a reaction inert solvent.

A preferred process within Process K, designated Process L, is wherein said temperature is about room temperature and which comprises the process wherein $R^2$ is t-butyldimethylsilyl and said fluoride source is tetrabutylammonium fluoride.

A preferred process within Process L, designated Process M, comprises the process wherein $R^3$ is acetyl and $R^4$ is methyl.

A preferred process within Process M, designated Process N, comprises the process wherein said compound of Formula IX-a is prepared from the compound of Formula VIII,

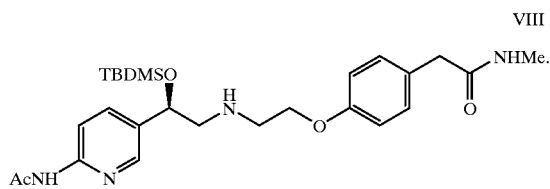

This invention is also directed to a process, designated Process O, for preparing a compound of Formula XII,

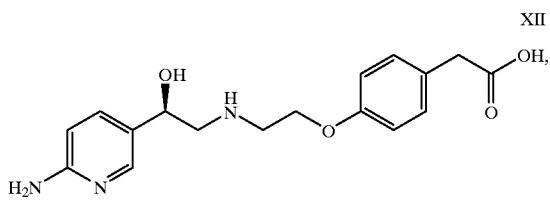

comprising reacting a compound of Formula III-a

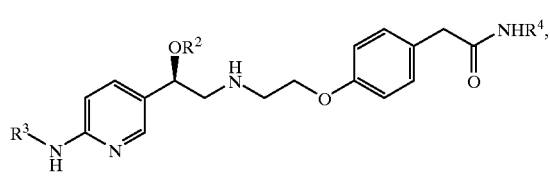

wherein $R^2$ is a silyl protecting group; $R^3$ is $(C_1-C_5)$ alkanoyl or benzoyl optionally substituted independently with up to three $(C_1-C_4)$alkyl, $(C_1-C_4)$alkoxy or halo and $R^4$ is $(C_1-C_8)$alkyl with aqueous base for about six hours to about thirty hours at about 90° C. to about 100° C. It will be appreciated by those skilled in the art that the time and temperatures required to effect this hydrolysis will be dependent upon the protecting groups being removed. Particularly preferred, when $R^3$ is acetyl and $R^4$ is methyl, is a time of 24 hours and a temperature of 100° C.

A preferred process within Process O comprises the process wherein the compound of Formula XII

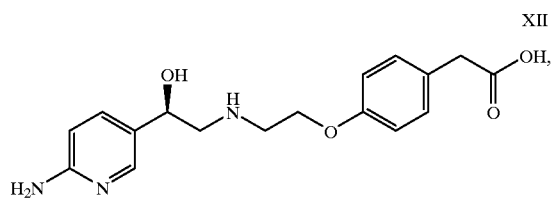

is prepared from the compound of Formula VIII,

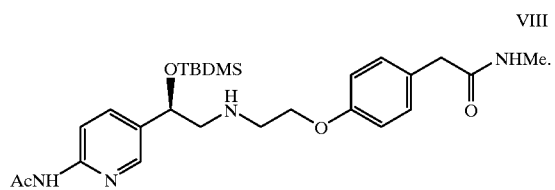

This invention is also directed to a process, designated Process P, for preparing a compound of Formula XII,

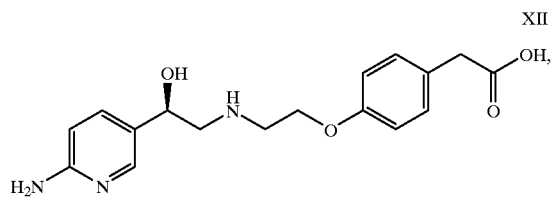

comprising:
(a) reacting a compound of Formula XIII,

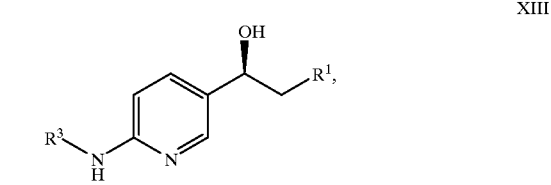

wherein $R^1$ is a leaving group selected from halo, toluenesulfonyloxy and methylsulfonyloxy; and $R^3$ is $(C_1-C_5)$alkanoyl or benzoyl optionally substituted independently with up to three $(C_1-C_4)$alkyl, $(C_1-C_4)$ alkoxy or halo, with a silylating agent and a first suitable base in a reaction inert solvent for a time of about 12 hours to about 18 hours at a temperature of about 20° C. to about 50° C. to form a compound of Formula XIV,

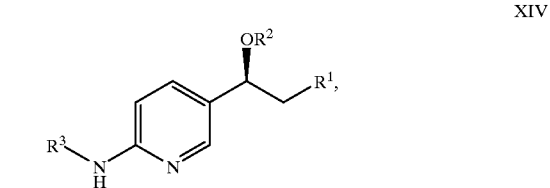

wherein $R^2$ is a silyl protecting group and $R^1$ and $R^3$ are as defined above;
(b) reacting said compound of Formula XIV with a compound of Formula VII,

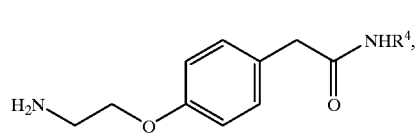

VII wherein $R^4$ is $(C_1-C_8)$alkyl and a second suitable base in a reaction inert solvent for a time of about six hours to about 24 hours at a temperature of about 60° C. to about 100° C. to form a compound of Formula XV,

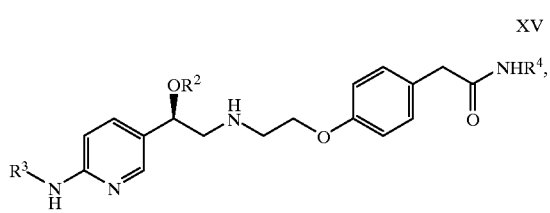

XV wherein $R^2$, $R^3$ and $R^4$ are as defined above;

(c) reacting said compound of Formula XV with a fluoride source in a reaction inert solvent for a time of about 6 hours to 12 hours at a temperature of about 0° C. to about 50° C. to form a compound of Formula XVI,

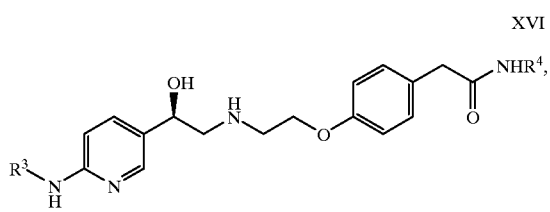

XVI wherein $R^3$ and $R^4$ are as defined above; and (d) reacting said compound of Formula XVI with aqueous base for a time of about six hours to about thirty hours at a temperature of about 90° C. to about 100° C. to form said compound of Formula XII.

A preferred process within Process P, designated Process Q, comprises the process wherein $R^1$ is toluenesulfonyloxy; $R^2$ is t-butyldimethylsilyl; $R^3$ is acetyl and $R^4$ is methyl.

A preferred process within Process Q comprises the process wherein in step (a), said silylating agent is t-butyldimethylchlorosilane and said first suitable base is imidazole; in step (b), said temperature is about 80° C., said time is about 18 hours and said second suitable base is dilsopropylethylamine; in step (c), said temperature is about room temperature and said fluoride source is tetrabutylammonium fluoride; and in step (d), said time is about 24 hours, said temperature is about 100° C. and said aqueous base is sodium hydroxide.

This invention is also directed to a process, designated Process R, for preparing a compound of Formula XII,

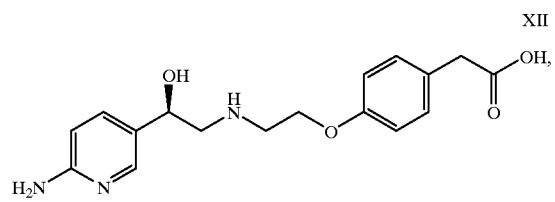

XII comprising:

(a) reacting a compound of Formula XIII,

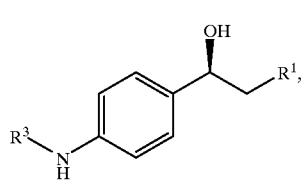

XIII wherein $R^1$ is a leaving group selected from halo, methanesulfonyloxy, benzenesulfonyloxy, p-toluenesulfonyloxy, m-nitrobenzenesulfonyloxy and p-nitrobenzenesulfonyloxy; and $R^3$ is $(C_1-C_5)$alkanoyl or benzoyl optionally substituted independently with up to three $(C_1-C_4)$alkyl, $(C_1-C_4)$alkoxy or halo, with a silylating agent and a first suitable base in a reaction inert solvent for a time of about 12 hours to about 18 hours at a temperature of about 20° C. to about 50° C. to form a compound of Formula XIV,

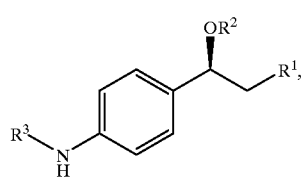

XIV wherein $R^2$ is a silyl protecting group and $R^1$ and $R^3$ are as defined above; and (b) reacting said compound of Formula XIV with a compound of Formula VII

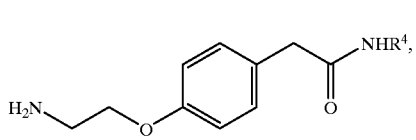

VII wherein $R^4$ is $(C_1-C_8)$alkyl and a second suitable base in a reaction inert solvent for a time of about 12 to about 18 hours at a temperature of about 60° C. to about 100° C. to form a compound of Formula XV,

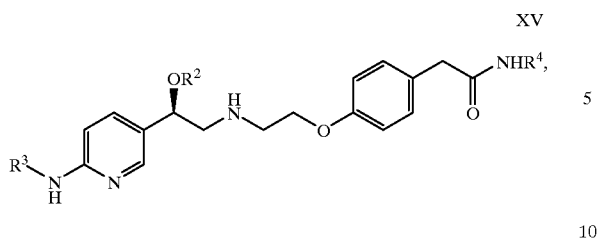

XV wherein $R^2$, $R^3$ and $R^4$ are as defined above; and (c) reacting said compound of Formula XV with aqueous base for a time of about six hours to about 24 hours at a temperature of about 90° C. to about 100° C. to form said compound of Formula XII.

A preferred process within Process R, designated Process S, comprises the process wherein $R^1$ is toluenesulfonyloxy; $R^2$ is t-butyldimethylsilyl; $R^3$ is acetyl and $R^4$ is methyl.

A preferred process within Process S comprises the process wherein in step (a), said silylating agent is t-butyldimethylchlorosilane and said first suitable base is imidazole; in step (b), said temperature is about 80° C. and said second suitable base is diisopropylethylamine; and in step (c) said time is about 24 hours, said temperature is about 100° C. and said aqueous base is sodium hydroxide.

This invention is also directed to a process, designated Process T, for preparing a compound of Formula XIIa,

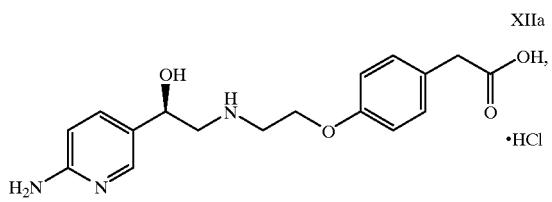

XIIa comprising:

(a) reacting a compound of Formula XIII,

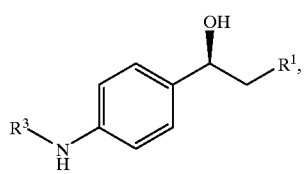

XIII wherein $R^1$ is a leaving group selected from halo, methanesulfonyloxy, benzenesulfonyloxy, p-toluenesulfonyloxy, m-nitrobenzenesulfonyloxy and p-nitrobenzenesulfonyloxy; and $R^3$ is $(C_1-C_5)$alkanoyl or benzoyl optionally substituted independently with up to three $(C_1-C_4)$alkyl, $(C_1-C_4)$alkoxy or halo, with a silylating agent and a first suitable base in a reaction inert solvent for a time of about 12 hours to about 18 hours at a temperature of about 20° C. to about 50° C. to form a compound of Formula XIV,

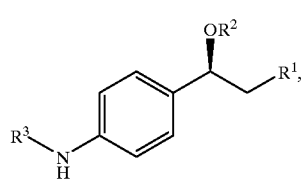

XIV wherein $R^2$ is a silyl protecting group and $R^1$ and $R^3$ are as defined above;

(b) reacting said compound of Formula XIV with a compound of Formula VII,

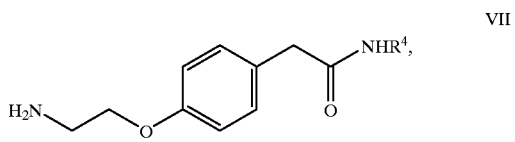

VII wherein $R^4$ is $(C_1-C_8)$alkyl and a second suitable base in a reaction inert solvent for a time of about 12 hours to about 18 hours at a temperature of about 60° C. to about 100° C. to form a compound of Formula XV,

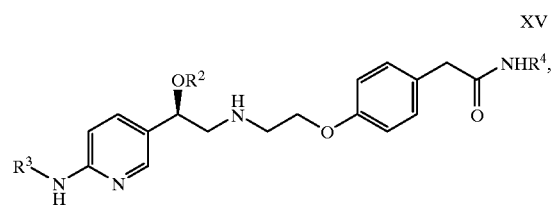

XV wherein $R^2$, $R^3$ and $R^4$ are as defined above;

(c) reacting said compound of Formula XV with aqueous base for a time of about six hours to about 30 hours at a temperature of about 90° C. to about 100° C. to form said compound of Formula XII,

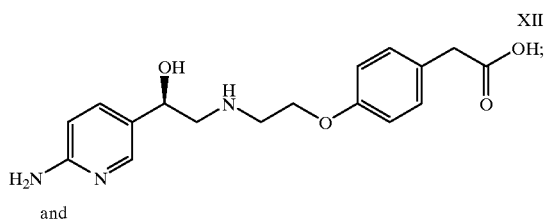

XII and (d) reacting said compound of Formula XII with HCl.

A preferred process within Process T, designated Process U, comprises the process wherein $R^1$ is toluenesulfonyloxy; $R^2$ is t-butyldimethylsilyl; $R^3$ is acetyl and $R^4$ is methyl.

A preferred process within Process U comprises the process wherein in step (a), said silylating agent is t-butyldimethylchlorosilane and said first suitable base is imidazole, in step (b), said temperature is about 80° C. and said second suitable base is diisopropylethylamine; and in step (c), said time is about 24 hours, said temperature is about 100° C. and said aqueous base is sodium hydroxide.

This invention is also directed to a process for purifying the zwitterionic form of the compound of Formula XII, comprising the steps of:

(a) forming a solution of an acid addition salt of said compound;

(b) adjusting the pH of said solution to within a range of between about 7.0 and about 7.5; and (c) collecting the zwitterionic crystals of said compound of Formula XII which form in said pH range.

It is noted that the capability for isolating compound XII by precipitation as the zwitterion represents a significant advantage in view of the relatively high aqueous solubility of salts (both acid addition and base addition) of compound XII. That is, the high aqueous solubility of such salts makes it difficult to isolate such salts in high yield by recrystallization, and isolation by evaporation is energy intensive. By isolating compound XII as the zwitterion, it is easily obtained in relatively high yields (typically about 90% and higher) without any of the aforementioned process difficulties.

Any pharmaceutically acceptable mineral or organic acid can be used to make an acid addition salt. Such adds include various mineral and organic acids such as hydrochloric, hydrobromic, hydriodic, sulfuric, phosphoric, acetic, trifluoroacetic, lactic, maleic, fumaric, citric, tartaric, succinic, and gluconic. The salt is made conventionally by adding an equivalent amount of the acid to the zwitterionic form, i.e., by (a) forming an aqueous solution and/or suspension of said compound of Formula XII (i.e., as the zwitterion); and (b) treating said aqueous solution or suspension with at least one equivalent (and up to two equivalents) of a pharmaceutically acceptable acid, thereby forming a suspension/solution of the resulting pharmaceutical salt. A di-acid salt can be formed, although mono-acid addition salts are also feasible. When making a solution (or suspension since the zwitterion has low aqueous solubility) of the compound of Formula XII, usually much of the zwitterion remains in suspended (undissolved) form until addition of the acid is commenced, due to the fact that the zwitterion has relatively low aqueous solubility. Initially undissolved zwitterion dissolves as acid is added to the solution.

Once the aqueous solution of an add addition salt of the compound of formula XII has been made, the solution is acidic. The solution can then be titrated to within the range of about 7.0 to about 7.5, at which point the compound of formula XII, in crystalline zwitterionic form, precipitates out of solution. The titration is conducted conventionally with a base, typically an aqueous alkali metal hydroxide such as lithium hydroxide, sodium hydroxide, or potassium hydroxide.

If desired, the aqueous solution of an acid addition salt of the compound of formula XII can be titrated directly to within the range of 7.0 to 7.5. Alternatively, the desired pH range of 7.0 to 7.5 can be "overshot", i.e., a pH above the desired range of 7 to 7.5 can be obtained by the titration. Typically a pH of 9 to 12 is obtained, thereby ensuring completeness of the neutralization reaction. Then the solution can be back titrated to a range of between 7.0 and 7.5 where the crystalline zwitterion precipitates and can be harvested. Typically a mineral acid such as HCl is employed for the back titration.

In a preferred embodiment this invention is directed to a process for purifying the zwitterionic form of the compound of Formula XII comprising (a) treating the zwitterionic form of the compound of Formula XII with one equivalent of hydrochloric acid in water to form a suspension of the hydrochloride salt of the compound of Formula XII;

(b) filtering said suspension of said hydrochloride salt of the compound of Formula XII to isolate said hydrochloride salt;

(c) suspending said hydrochloride salt in water to form a suspension; and (d) adjusting said suspension to a pH of 9 to 12 by adding base and titrating said solution to pH 7 by adding acid.

In an especially preferred embodiment for purification of the zwitterion, the hydrochloride salt of the compound of Formula XII is made by adding aqueous HCl to the zwitterionic form of compound XII until a pH of about 3 is obtained, thereby forming an HCl addition salt (likely as a mixture of mono-HCl and di-HCl salts). The pH of the solution is then adjusted to about 7.0 to 7.5 by titrating with aqueous sodium hydroxide. At this point, and optionally, the zwitterion crystals which form at pH 7.0 to 7.5 may be treated by the following process: (i) the crystals may be filtered and the filtrate discarded; (ii) additional aqueous base may be added to the filtered crystals from (i) until a solution having pH of about 11–12 is obtained; (iii) the resulting solution from (ii) may be titrated with aqueous acid (e.g., HCl) back to a pH in the range of about 7.0 to about 7.5: and (iv) the resulting solution may be filtered to obtain the zwitterion and the filtrate discarded. One further equivalent of aqueous sodium hydroxide is then added to the zwitterion (crystals or solution), thereby changing the pH to about 11–12. Aqueous HCl is then used to titrate the solution back to a pH of about 7.0 to 7.5, whereby zwitterionic crystals of compound XII are formed and the solution is transformed into a slurry or suspension containing the poorly soluble zwitterion.

A final purification step can then be implemented, wherein an equivalent of HCl is first added to the slurry or suspension to re-form the HCl salt. The salt solution is then titrated with aqueous NaOH up to a pH of about 9–12, and then titrated back down to a pH of about 7.0 to about 7.5 using aqueous HCl. The crystals can be harvested by conventional filtration.

The zwitterionic crystals thereby produced by the processes discussed above are formed in a preferred polymorph of this invention, referred to herein and in the claims as "Form B", and is characterized by the major peaks in the following X-ray diffraction pattern.

| Peak No. | 1 | 2 | 3 | 4 | 5 | 6 | 7 | 8 | 9 | 10 |
|---|---|---|---|---|---|---|---|---|---|---|
| $2\Theta(°)$ Cu | 13.2 | 18.5 | 20.1 | 20.4 | 21.1 | 25.0 | 25.2 | 25.7 | 29.6 | 30.2 |
| I rel | 24.1 | 22.0 | 100 | 83.0 | 51.9 | 28.8 | 30.2 | 36.4 | 19.0 | 11.4 |
| d space (A) | 6.7 | 4.8 | 4.4 | 4.3 | 4.2 | 3.6 | 3.5 | 3.5 | 3.0 | 3.0 | wherein relative intensities (I(rel)) are also shown for convenience. In differential scanning calorimetry (DSC), Form B is additionally characterized, relative to Form A discussed below, by a distinct, single melt temperature of 205° C.

Polymorph Form B can be formulated to treat a mammal, including a human, for any of the conditions disclosed in PCT application PCT/IB95/00344, which was published Nov. 14, 1996 as WO 96/35671, and which is herein incorporated by reference. The polymorph can be formulated as a composition in the form of any of the dosage forms disclosed in the aforementioned published application, and can include excipients conventionally employed in the formulation arts. Such dosage forms are compositions comprising an amount of polymorph Form B effective to treat the particular condition, and an a pharmaceutically acceptable carrier or diluent. An effective amount of polymorph form B is an amount as disclosed in the aforementioned WO 96/35671, and will generally be a daily dose in the range of 0.01 to 100 mg/kg of body weight.

A second polymorph of the compound of Formula XII, herein designated as Form A, also exists and results from the synthetic procedures disclosed in commonly assigned application PCT/IB97/01367, published internationally on Nov. 3, 1997 as WO 98/21184. It is characterized by the major peaks in the following X-ray diffraction pattern.

| Peak No. | 1 | 2 | 3 | 4 | 5 | 6 |
|---|---|---|---|---|---|---|
| 2Θ(°) Cu | 20.0 | 21.1 | 22.0 | 25.5 | 25.8 | 29.8 |
| I (rel) | 100 | 55.9 | 13.6 | 34.3 | 44.6 | 14.1 |
| d space (A) | 4.4 | 4.2 | 4.4 | 3.4 | 3.4 | 3.0 |

Form A is additionally characterized by a DSC melt lower than that of Form B. The DSC reveals a melt at 170 C followed by a second event at 195 C.

Thus the polymorphic zwitterionic forms of compound XII are easily distinguishable from each other by their x-ray patterns and DSC melts.

DETAILED DESCRIPTION OF THE INVENTION

A process for the manufacture of a compound of Formula XII as defined above is provided as a feature of the invention and is illustrated by the following procedure, set forth in Scheme 1, in which the meanings of generic radicals are as described above unless otherwise specified.

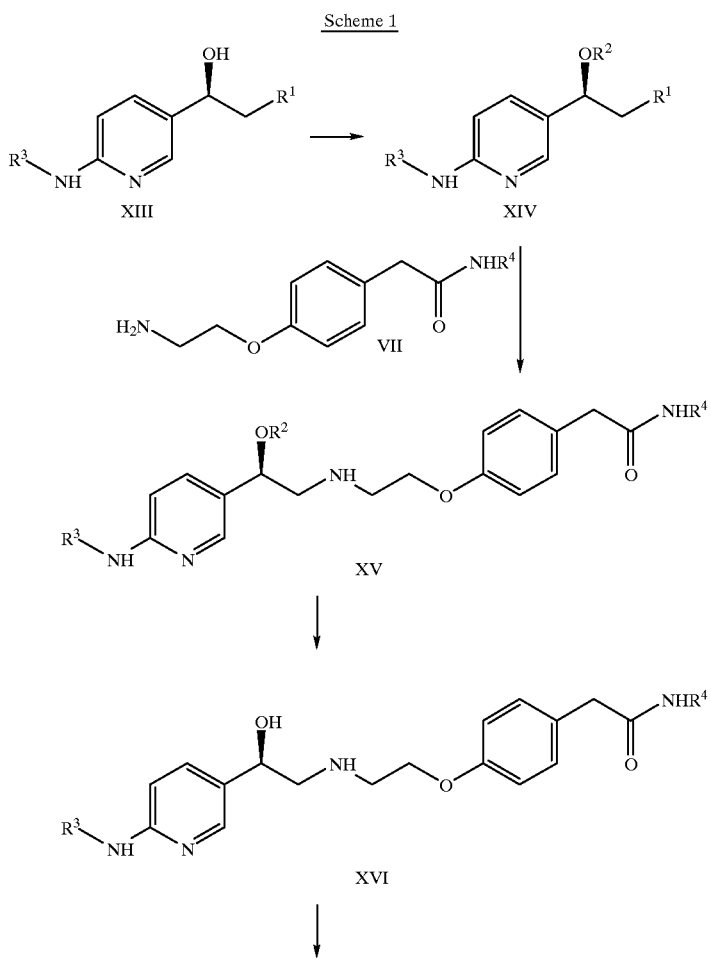

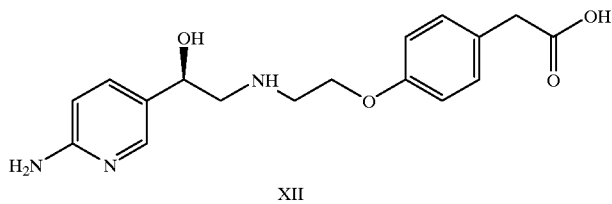

XII

Processes for the manufacture of a compound of Formula XII as defined above are illustrated by the following procedures.

The compounds of Formula XII are synthesized from compounds of Formula XVI by reaction with aqueous alkali hydroxide for a sufficient time to hydrolyze the two amide groups. It will be appreciated by those skilled in the art that the time and temperatures required for this hydrolysis reaction will be dependent upon the protecting groups being removed. This reaction is typically carried out by reacting the hydrochloride salt of the compound of Formula XVI with an excess of sodium hydroxide in water at about 90° C. to about 100° C., or, convenienty, at reflux, for about six hours to about thirty hours. It is particularly preferred, when $R^3$ is acetyl and $R^4$ is methyl, to heat the reaction mixture at about 100° C. for about 24 hours. The compound of Formula XII can be isolated as its zwitterion, e.g.,

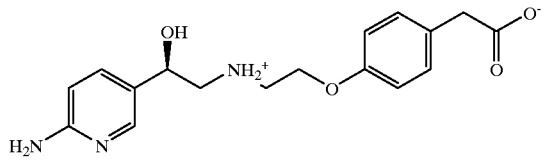

or as a mono-hydrochloride salt by proper adjustment of the pH of the aqueous solution. The mono-hydrochloride salt process has the advantage that trace impurities which sometimes co-precipitate with the zwitterion can be separated from the product.

Alternatively, the compound of Formula XII is prepared by heating a compound of Formula XV wherein $R^2$ is a trialkylsilane moiety in aqueous alkali hydroxide. In this instance, the initial basic aqueous reaction mixture is filtered to remove the bulk of the silicon containing residues which precipitate during the course of the reaction.

The compounds of Formula XVI are prepared by treating a compound of Formula XV wherein $R^2$ is trialkylsilyl with a fluoride reagent in a reaction inert solvent. This reaction may be carried out at a temperature of from about 0° C. to about 50° C. for about six hours to about twelve hours. Conveniently, the reaction is carried out at room temperature in tetrahydrofuran. The compounds of Formula XVI are isolated from the reaction by the introduction of sufficient hydrochloric acid to precipitate the product as a hydrochloride salt. This provides a convenient method to aid in the purification of compounds of Formula XVI. The preferred fluoride reagent is tetrabutyl ammonium fluoride.

The compounds of formula XV are prepared by treating a compound of Formula XIV with an excess (generally two equivalents) of a primary amine of Formula VII in a reaction inert solvent for about six hours to about 24 hours at a temperature of about 60° C. to about 100° C. Typically, the optimum temperature for this reaction is 80° C. Generally this reaction is carried out in the presence of a suitable tertiary amine base. Suitable bases include but are not limited to triethylamine, N-methylmorpholine, pyridine, 2,6-lutidine, N,N-diisopropyl-ethylamine or excess (e.g., three equivalents) compound of Formula VII. A preferred base is N,N-diisopropylethylamine. With respect to this particular reaction, it is preferred that the solvent is a polar, non-hydroxylic solvent such as dimethylformamide, dimethyl acetamide, N-methyl pyrrolidinone or dimethylsulfoxide. Generally the most preferred solvent is dimethylsulfoxide.

A particular advantage of the compounds of Formula XV of this invention as intermediates is the solubility of those compounds in organic solvents. The high water solubility of the intermediates used in previous processes to prepare the compound of Formula XII required the protection of the secondary nitrogen atom with a lipophilic protecting group to allow extraction of the desired intermediate from the crude reaction mixture. This required protection and deprotection steps, adding two steps to the overall synthesis. The compounds of Formula XV of this invention are easily isolated and therefore require no additional steps to allow easy isolation and further processing. In addition, the previous processes used to prepare the compound of Formula XII utilized epoxide intermediates which have been found to be prone to both racemization of the chiral center and opening at the undesired benzylic carbon atom of the epoxide. These tendencies were particularly noticeable at larger scale. Furthermore, it has been found that the acidic hydrolyses used in previous processes to prepare the compound of Formula XII surprisingly caused some racemization of the chiral alcohol center especially at large scale. Both the reaction of amine of Formula VII at the benzylic carbon center and racemization of the chiral center does not occur in the current invention.

The compounds of Formula XIV are prepared by treating a compound of Formula XIII wherein $R^1$ is as defined above with a silylating agent in a reaction inert solvent in the presence of a suitable base at about 0° C. to about 50° C. for about 12 hours to about 18 hours. The preferred $R^1$ group is p-toluenesulfonyloxy. Suitable silylating agents include but are not limited to trialkylchlorosilanes such as triethylchlorosilane, t-butyl-dimethyl-chlorosilane, triisopropylchlorosilane and alkyl-arylchlorosilanes such as diphenylmethyl-chlorosilane. A preferred silylating agent is t-butyl-dimethyl-chlorosilane. Suitable bases include but are not limited to triethylamine, N,N-diisopropylethylamine, imidazole, pyridine, 2,6-lutidine, and N-methyl-morpholine. A preferred base is imidazole. Suitable reaction inert solvents include dimethylacetamide, tetrahydrofuran, dimethylformamide, methylene chloride and chloroform. A preferred solvent is dimethylformamide. Silylation reactions are described in E. J. Corey and J. O. Link [J. Organic Chemistry, 56, 443 (1991)] and P. R. Brodfuehrer et al. [Organic Process Research and Development, 1, 176 (1997)].

Alternatively, a compound of Formula XIV wherein $R^2$ is tetrahydropyranyl is obtained by reaction of a compound of Formula XIII with dihydropyran in a reaction inert solvent such as methylene chloride in the presence of an acid catalyst such as toluenesulfonic acid.

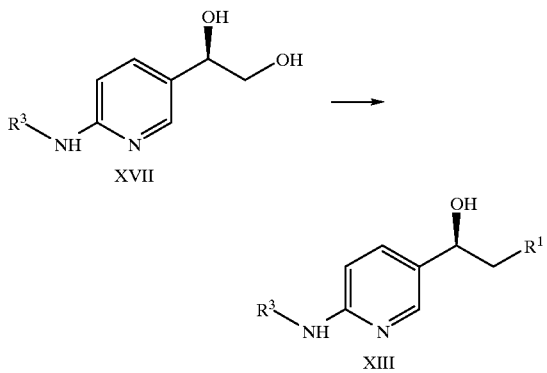

When the compounds of Formula XIII are organosulfonyloxy derivatives, said compounds may be prepared by reacting an appropriate compound of Formula XVII with an organosulfonyl chloride in the presence of a suitable base. Suitable bases which may be used to effect this transformation include the lower trialkylamines, pyridine and pyridine derivatives. Preferred bases within those groups include but are not limited to triethylamine, diisopropylethylamine, pyridine, 2,4,6-collidine and 2,6-lutidine. Pyridine is the most preferred base. Suitable organosulfonyl chlorides include methanesulfonyl chloride, p-nitrobenzenesulfonyl chloride, m-nitrobenzenesulfonyl chloride, p-toluenesulfonyl chloride and benzenesulfonyl chloride. A generally preferred organosulfonyl chloride derivative is p-toluenesulfonyl chloride. The reaction is conveniently conducted by stirring the desired substrate compound of Formula XVII together with the appropriate organosulfonyl chloride in a reaction inert solvent at a temperature of about 20° C. to about 50° C. It is preferred that the solvent is a polar solvent such as an ether derivative including but not limited to tetrahydrofuran, dioxane and dimethoxyethane; chlorinated hydrocarbons including but not limited to carbon tetrachloride, chloroform and methylene chloride; aromatic hydrocarbons including but not limited to benzene, toluene and xylene;

dimethylformamide; N-methyl-2-pyrrolidinone; dimethylacetamide; pyridine or any mixture of these solvents. Generally the most preferred solvent is pyridine.

To prepare the compounds of Formula XIII wherein $R^1$ is halo, the 2-organosulfonyloxy derivatives of the compound of Formula XIII or mixtures thereof containing 2-chloro derivatives of the Formula XIII are reacted with a halogenating agent in a reaction inert solvent. The reaction may be conducted conveniently at a temperature of from about 25° C. to the reflux temperature of the solvent utilized. It is generally preferred to conduct the reaction at the reflux temperature. Halogenating agents are compounds which are capable of transferring a halo group to an organic substrate, said substrate having a leaving group which can be displaced by said halide ion. Preferred halogenating agents are lithium halides. A particularly preferred chlorinating agent used to prepare the compounds of formula XVII is lithium chloride. A preferred solvent is ethanol.

The preparation of the compounds of Formula XVII and the compound of Formula VII has been described in International Patent Publication Number WO98/21184. Those compounds may be prepared as set forth in the preparation section below. Specifically, the compound of Formula XVII wherein $R^3$ is acetyl is prepared as set forth in Preparation Two below. For example, the compound of Formula VII wherein $R^4$ is methyl is prepared as set forth in Preparation Seven below. Other compounds of Formula VII may be prepared by methods analogous thereto.

It will be appreciated by those skilled in the art that the compound of Formula IX contains two basic nitrogen atoms and that under certain conditions used to precipitate the compound of Formula IX as a salt, e.g., where more than two equivalents of add are used, the compound of Formula IX may form a dihydrochloride salt. Said dihydrochloride salt can be used in subsequent steps in the processes of this invention and is within the scope of the processes of this invention.

It will be appreciated by those skilled in the art that the compounds of Formulas XII, XIII, XIV, XV and XVI contain at least one chiral center. Accordingly, those compounds may exist in, and be isolated in, optically active and racemic forms. Some compounds may exhibit polymorphism. It is to be understood that the present invention encompasses any racemic, optically active, polymorphic or stereoisomeric form, or any, mixture thereof, which form possesses properties useful in the treatment of the diseases or conditions noted herein or useful as intermediates in the preparation of any compounds useful in the treatment of said diseases or conditions, it being well known in the art how to prepare optically active forms (for example, by resolution of the racemic form by recrystallization techniques, by synthesis from optically active starting materials, by chiral synthesis or by chromatographic separation using a chiral stationary phase) and how to determine efficacy for the treatment of said utilities. In general, (R)-stereochemistry is preferred at all chiral centers in the compounds disclosed in this invention.

Conventional methods and techniques of purification and separation known to those skilled in the art may be used to isolate the compounds of this invention. Such techniques include all types of chromatography, including but not limited to high performance liquid chromatography, column chromatography using common adsorbents such as silica gel, thin layer chromatography and the like; recrystallizaton; and differential (i.e., liquid—liquid) extraction techniques.

As used in the specification and appendant claims the following terms have the meanings described. The terms "alkyl", "alkoxy" and "alkanoyl" include both straight and branched chain radicals, but it is to be understood that references to individual radicals such as propyl or propoxy embrace only the straight chain radical unless reference is specifically made to for example isopropyl or isopropoxy, in which case the branched chain isomer is meant.

The term "halo", unless otherwise indicated, includes chloro, fluoro, bromo and iodo.

The term "suitable leaving group" includes a group which may be readily displaced by a nucleophile which has a greater affinity for the positively charged carbon atom to which said leaving group is attached than said leaving group. Preferred leaving groups are chloro and organosulfonyloxy groups. Particularly preferred leaving groups are organosulfonyloxy groups. Particularly preferred organosulfonyloxy groups are methanesulfonyloxy, benzenesulfonyloxy, p-toluenesulfonyloxy, p-nitobenzenesulfonyloxy or m-nitrobenzenesulfonyloxy.

The term "suitable base" includes a base which, when added to the reaction mixture in which said base is to operate, increases the pH of the reaction mixture or operates on the substrate to remove a proton from said substrate or otherwise render said substrate susceptible to electrophilic attack without affecting other potentially reactive functional groups in said substrate.

The term "silyl protecting group" means a silicone moiety which is attached to an oxygen atom of the substrate forming a silyloxy compound, wherein the bond between the silicone and oxygen atoms is easily cleaved under standard deprotecting conditions. Preferred silylating agents are silyl chlorides.

The expressions "reaction inert solvent" and "inert solvent" refer to a solvent which does not interact with starting materials, reagents, intermediates or products in a manner which adversely affects the yield of the desired product. Further, the term reaction inert solvent may refer to a single, dual or multiple solvent system depending upon the nature of the reaction and the solubility of the substrate and/or reagents being disclosed.

The expression "pharmaceutically-acceptable salts" is intended to include but not be limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts.

The acid addition salts of the compounds of the present invention are readily prepared by reacting the base forms of the compounds disclosed in this invention with an appropriate acid. When the salt is of a monobasic acid (e.g., the hydrochloride, the hydrobromide, the p-toluenesulfonate, the acetate) the hydrogen form of a dibasic add (e.g., the hydrogen sulfate, the succinate) or the dihydrogen form of a tribasic add (e.g., the dihydrogen phosphate, the citrate), at least one molar equivalent and usually a molar excess of the acid is employed. However, when such salts as the sulfate, the hemisuccinate, the hydrogen phosphate or the phosphate are desired, the appropriate and exact chemical equivalents of acid will generally be used. The free base and the acid are conveniently combined in a co-solvent from which the desired salt precipitates or can otherwise be isolated by concentration and addition of a non-solvent or by simple addition of a non-solvent without concentration or by lyophilization of an aqueous solution of said salt.

If not commercially available, the necessary starting materials for the chemical reactions disclosed herein may be prepared by procedures which may be selected from standard organic chemical techniques found in standard organic chemistry textbook references. The techniques found therein may be applied directly to the synthesis of known starting materials described directly in that reference or may be applied by analogy to compounds having similar functionality to achieve predictable results.

In this specification the following abbreviations and acronyms are used with the following meanings:

Ts, meaning toluenesulfonyl;

TBDMS, meaning t-butyldimethylsilyl;

THF, meaning tetrahydrofuran;

DMF, meaning N,N-dimethylformamide;

NMP, meaning N-methyl-2-pyrrolidinone;

DMAC, meaning N,N-dimethylacetamide;

DMSO, meaning dimethylsulfoxide; and

TFA, meaning trifluoroacefic acid.

The present invention is illustrated by the following Examples. However, it should be understood that the invention is not limited to the specific details of these Examples.

Example One

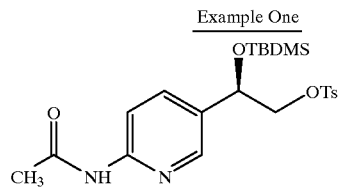

Toluene-4-sulfonic Acid 2(R)-(6-acetylamino-pyridin-3-yl)-2-(tert-butyl-dimethyl-silyloxy)-ethyl Ester.

Toluene-4-sulfonic acid 2(R)-(6-acetylamino-pyridin-3-yl)-2-(hydroxy)ethyl ester (the compound of Preparation Three, 1000 g, 2.85 moles) and imidazole (388.5 g, 5.7 moles) were dissolved in dry dimethylformamide (1 L) with cooling in an ice water bath under a nitrogen atmosphere. To the resulting amber solution was added t-butyldimethylchlorosilane (559 g, 3.7 moles) over a 10 minute period. The reaction temperature slowly rose to 35° C. over the next 40 minutes. The mixture was stirred at room temperature for 18 hours. Ethyl acetate (8 L) and water (4 L) were added to the reaction. The layers were separated and the ethyl acetate layer was washed 1× water (4 L). The organic layer was separated and concentrated by distillation under vacuum to less than 2 L volume at which point a slurry had formed. Hexanes (4 L) were added to the warm slurry and mixture was cooled to 5° C. and stirred for 3 hours. The crystalline product was isolated by filtration and washed with cold hexanes. The yield of white solids after vacuum drying was 1059 g, 80%. mp 121–124° C. $[a]_D$–48.9 (c=1.01, MeOH). $^1$NMR (400 MHz, DMSO-$d_6$) δ=10.42 (s, 1), 8.16 (s, 1), 7.93 (d, 1, 8.7 Hz), 7.7–7.59 (m, 3), 7.37 (d, 2), 4.93 (t, 1), 4.00 (s, 2), 3.28 (s, 1), 2.35 (s, 3), 2.03 (s, 3), 0.73 (s, 9), –0.04 (s, 3), –0.19 (s, 3).

Example Two

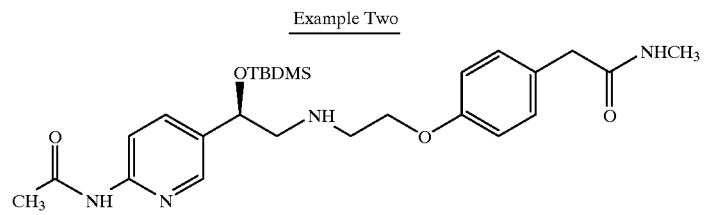

2-(4-{2-[2-(6-Acetylamino-pyridin-3-yl)-2(R)-(t-butyldimethylsilyloxy)-ethylamino]-ethoxy}phenyl)-N-methyl-acetamide.

Toluene-4-sulfonic acid 2-(6-acetylamino-pyridin-3-yl)-2(R)-(tert-butyl-dimethyl-silyloxy)-ethyl ester (the compound of Example One, 200 g, 0.43 moles) and 4-(2-aminoethoxy)-N-methylbenzene acetamide (179.1 g, 0.86 moles) were combined in dry dimethylsulfoxide (130 ml).

To this mixture under nitrogen was added N,N-diisopropylethylamine (55.6 g, 0.43 moles) in one portion. The reaction was heated to 80° C. during which it became an amber solution. The reaction was heated at this temperature for 17 hours. The reaction mixture was cooled to 35° C. and water (784 ml) was added followed by ethyl acetate (874 ml). This was stirred for 10 min, then the layers separated and the organic layer was washed twice more with water (200 ml each). The organic layer was dried over sodium sulfate, filtered and concentrated to give crude 2-(4-{2-[2-(6-acetylamino-pyridin-3-yl)-2(R)-(t-butyldimethylsilyl-oxy)ethylamino]-ethoxy}phenyl)-N-methyl-acetamide. A purified sample was obtained by column chromatography (silica gel, 5% MeOH/CHCl$_3$). [a]$_D$ –52.3 (c=1.04, CHCl$_3$). NMR (300 MHz, CDCl$_3$) δ=8.64 (s, 1), 8.23 (s, 1), 8.17 (d, 1), 7.69 (d, 1), 7.14 (d, 2), 6.86 (d, 2), 5.48 (bs, 1), 4.86 (m, 1), 4.06 (t, 2), 3.50 (s, 2), 3.01 (t, 2), 2.90 (t, 1), 2.74 (m, 4), 2.20 (s, 3), 0.90 (s, 9), 0.1 (s, 3), –0.4 (s, 3). Mass spectrum: m/e: 500 (M$^+$).

2-(4-{2-[2-(6-Acetylamino-pyridin-3-yl)-2(R)-hydroxy-ethylamino]-ethoxy}-phenyl)-N-methyl-acetamide hydrochloride (the compound of Example Three, 50 g, 0.11 moles) was dissolved in water (236 ml) and stirred while a solution of sodium hydroxide (21.8 g, 0.545 moles) in water (98 ml) was added over a ten min period. The reaction was heated to 98–100° C. on a steam bath and held at that temperature for 24 hr. Darco® G-60 (5 g) was added to the warm reaction which was stirred for 30 min, then filtered through Celite® to remove the Darco®. The filter cake was washed with hot water (50 ml). The aqueous filtrate was cooled to 10° C. and the pH was adjusted with conc. HCl (about 19 ml) from pH 12.5 to pH 7.0. The resulting slurry was stirred for 3 hr. The solids were collected by filtration and washed well with water followed by THF (100 ml). The crude product was dried in vacuo to provide 26.4 g, a 73% yield. The crude solids were purified by an acid/base process. The material (50 g, 0.15 moles) isolated as described from the basic hydrolysis was slurried in water (200 ml). To the slurry was Example Three

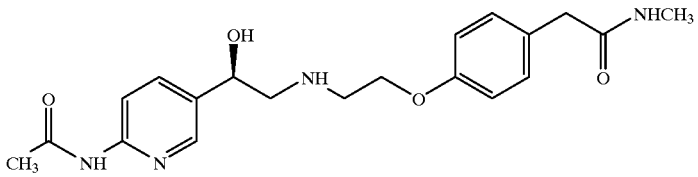

2-(4-{2-[2-(6-Acetylamino-pyridin-3-yl)-2(R)-hydroxy-ethylamino]-ethoxy}-phenyl)-N-methyl-acetamide hydrochloride.

The ethyl acetate solution from Example 2 was concentrated in vacuo without drying to provide the crude oil. This was dissolved in toluene (336 ml) and reconcentrated to remove ethyl acetate and the resulting oil was dissolved in dry tetrahydrofuran (1400 ml). The THF solution was stirred under nitrogen while a solution of 1M tetrabutylammonium fluoride in THF was added over 15 min. The reaction was stirred overnight at room temperature. The mixture was cooled to less than 10° C. and treated with ethanolic hydrochloric acid prepared by careful addition of acetyl chloride (91.75 ml) to ethanol (250 ml) with cooling in a separate reactor. After the hydrochloric acid addition, the slurry was stirred for 1 hr at less than 10° C. The resulting solids were collected by filtration under nitrogen to prevent the uptake of moisture and washed with THF (500 ml), followed by isopropyl ether (2×1 L). The solids were pulled dry and transferred to a clean flask and stirred with acetonitrile (1792 ml) at room temperature overnight. The solids were collected by filtration and washed with acetonitrile (1 L) followed by isopropyl ether (2×500 ml). The white solid was dried in vacuo at 45° C. to 50° C. to provide the title compound as its hydrochloride, 164 g, 83% yield.

added conc. HCl (24.9 ml, 0.3 moles) to get a hazy solution. The solution was filtered through Celite® to remove the haze and the cake was washed with water. The pH of the filtrate was adjusted with 10% NaOH to pH 8.0 and stirred overnight. In the morning, the pH had drifted to 6.7. More NaOH solution was added to achieve a stable pH of 7.0. A total of about 135 ml of 10% NaOH was used. The overnight stirring before the final adjusting of the pH was instituted due to the buffering capacity of the compound and in particular the slow conversion of the highly crystalline mono-hydrochloride salt to the zwitterion. The solids were collected by filtration and redissolved in water (250 ml) with NaOH (6 g, 0.15 moles). The resulting hazy solution was filtered through Celite®. The filtrate was adjusted to pH 7.0 with 3N HCl (about 44 ml) to give the purified zwifteron which was filtered off and dried in vacuo at 45° C. The yield for the purification was 71.6%, 35.8 g; mp 207–208° C. (dec.) NMR (300 MHz, D$_2$O+DCl) δ=7.93 (d, 1), 7.86 (s, 1), 7.28 (d, 2), 7.05 (d, 1), 7.00 (d, 2), 5.10 (dd, 1), 4.34 (t, 2), 3.69 (s, 2), 3.60 (t, 2), 3.40 (m, 2).

Example Five

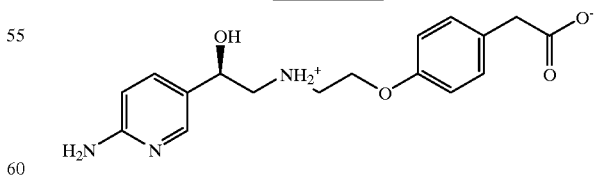

(4-{2-[2-(6-Amino-pyridin)-3-yl)-2(R)-hydroxy-ethylamino]-ethoxy}-phenyl)-acetic Acid.

2-(4-{2-[2-(6-Acetylamino-pyridin-3-yl)-2(R)-(t-butyldimethylsilyloxy)-ethylamino]-ethoxy}-phenyl)-N-methyl-acetamide (the compound of Example Two, 19.6 g, 39 mmoles in toluene (60 ml)) was combined with water Example Four

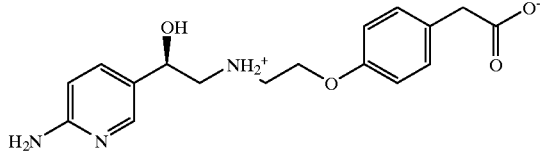

(4-{2-[2-(6-Amino-pyridin-3-yl)-2(R)-hydroxy-ethylamino]-ethoxy}-phenyl)-acetic Acid.

(196 ml) and evaporated to remove most of the toluene in vacuo. To the slurry of oily silyl ether and water was added sodium hydroxide (8.7 g, 21.8 mmoles). The mixture was heated to reflux and the residual toluene was removed and the volume reduced to about 120 ml. After the reaction was judged complete by thin layer chromatography (silica gel, 10% methanol in chloroform as eluant), Darco® G-60 (4.5 g) was added and the reaction was cooled to room temperature. The slurry was filtered through Celite® to remove the silicon containing by-products which precipitated from the aqueous mixture. The filtrate was acidified with conc. HCl to pH 7.0 to precipitate the crude product. The product was purified by first dissolving in aqueous HCl at pH 1–2 and filtering off insolubles. The product was precipitated by addition of NaOH to pH 7.0. This was followed by the basic dissolution—filtration and crystallization at pH 7.0. Ten grams of crude amino acid from this procedure gave 4.13 g of purified product, 41.3% recovery. If further purification was needed the material was recrystallized from hot water or dimethylformamide. This was identical with that from Example 4.

Example Six

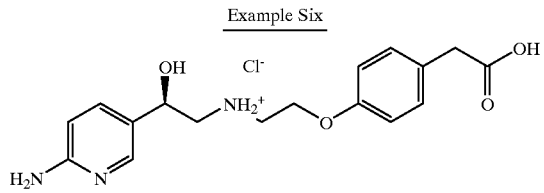

(4-{2-[2-(6-Amino-pyridin-3-yl)-2(R)-hydroxy-ethylamino]-ethoxy}phenyl)-acetic Acid Mono-hydrochloride Salt.

(4-{2-[2-(6-Amino-pyridin-3-yl)-2(R)-hydroxy-ethylamino]-ethoxy}-phenyl)-acetic acid (prepared according to the procedure set forth in Example Five, 1035 g, 3.123 moles) was suspended in water (5.175 L) at room temperature. Conc. hydrochloric acid (36%, 258 ml, 3.123 moles) was added over a 5–10 minute period which caused a slight rise in the temperature. This caused partial dissolution of the zwitterion and precipitation of the mono-hydrochloride salt. After stirring overnight, the solids were collected, washed with tetrahydrofuran and dried to give the title salt, 988 g, 86.1% yield. The hydrochloride salt (983 g, 2.67 moles) was suspended in 9.83 liters of water. The pH was adjusted to about pH 9.1 with 10% sodium hydroxide solution (1 liter) to give a solution. The pH was then adjusted to about 7.0 with conc. HCl. The resulting precipitate of the zwitterion form of the compound was collected by filtraton, washed with water and tetrahydrofuran. After drying in vacuo, the compound weighed 823 g, 78% yield. The spectral properties were identical with those set forth in Example Five.

This procedure is useful for the removal of trace impurities from the crude product which co-precipitate with the zwitterion.

EXAMPLE 7

This example illustrates formulations of a compound of Formula XII.

Film coated tablets containing 25, 100, and 200 mg of Compound XII, as polymorph Form B, were prepared. The composition of the tablets is given in the following table

| | Component | mg/Tablet (25 mgA) | mg/Tablet (100 mgA) | mg/Tablet (200 mgA) |
|---|---|---|---|---|
| 1. | Formula XII | 25 | 100 | 200 |
| 2. | Microcrystalline Cellulose (Avicel ® PH200) | 200 | 367.5 | 267.5 |
| 3. | Microcrystalline Cellulose (Avicel ® PH200) | 245 | — | — |
| 4. | Sodium Croscarmellose (Ac-Di-Sol ®) | 25 | 25 | 25 |
| 5. | Magnesium Stearate | 2.5 | 5.0 | 5.0 |
| 6. | Magnesium Stearate | 2.5 | 2.5 | 2.5 |
| 7. | White Opadry ® I (YS-1-18027-A) | 15 | 15 | 15 |
| 8. | Clear Opadry ® I (YS-1-19025-A) | 1.25 | 1.25 | 1.25 |
| | Total Weight (core) | 500 mg | 500 mg | 500 mg |
| | Total Weight (tablet) | 516.25 mg | 516.25 mg | 516.25 mg |

The tablets were made by screening each of the compound of formula XII, microcrystalline cellulose (item 2), and sodium croscarmellose (item 4) through a 40 mesh sieve, followed by mixing and blending the mixture for 10 minutes in a S/S twin shell V-blender. Any remaining microcrystalline cellulose (item 3) was added at this point and blending was continued for an additional 10 minutes. Magnesium stearate was added and blending continued for 5 minutes. The resulting mixture was then roller compacted using a roller pressure of 40 kg/cm³ and granulated in a rotary granulator with #20 mesh and an auger speed of 16 rpm. Blending was then continued for 10 minutes. Additional magnesium stearate (item 6) was then added and blending continued for 5 minutes. Tablets were then made on a Killian T-100 tablet press (30,000 tablets/hr) using 0.25"×0.5625" capsular tooling. The tablets were then film coated in a HCT30 coating pan using an aqueous Opadry®I YS-1-18027-A (white) (item 7) spray solution at a concentration of 15%, and employing the following conditions: pan speed: 20 rpm; inlet temperature: 58° C.; Outlet temperature: 40° C.; Spray rate: 5.5–5.8 g/min. An additional clear film coat of Opadry®YS-1-19025-A (item 8) was then applied (5% aqueous concentration) under the following conditions: pan speed: 20 rpm; inlet temperature: 60° C.; Outlet temperature: 40° C.; Spray rate: 5.7–5.9 g/min.

Preparation One

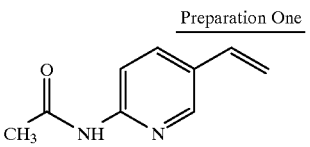

N-(5-Vinyl-pyridin-2-yl)-acetamide.

A solution of N-(5-bromo-pyridin-2-yl)-acetamide (4.30 g, 20 mmol) in acetonitrile (15 ml) and triethylamine (5.04 ml) was treated with palladium acetate (45 mg, 0.2 mmol) and triotolylphosphine (203 mg, 0.66 mmol). The mixture was placed in a pressure reactor under 50 psig of ethylene pressure and heated at 85° C. for 66 hours. The reaction mixture was cooled, vented, and partitioned between phosphate buffer (0.1 M, pH 6.6) and ethyl acetate. The aqueous phase was extracted with ethyl acetate twice more. The combined ethyl acetate extracts were washed with additional phosphate buffer, brine and dried over sodium sulfate. The extracts were filtered and evaporated to afford 2.06 g (63%)

of the title product as a flaky crystalline residue. Recrystallization from ethyl acetate/cydohexane gave colorless flakes. mp 120–121° C. 1H NMR (CDCl$_3$): δ=8.55 (br, 1 H); 8.24 (d, 1 H); 8.15 (d, 1 H); 7.76 (d of d, 1H); 6.64 (d of d, 1 H); 5.73 (d, 1 H); 5.28 (d, 1 H); 2.19 (s, 3 H). MS (Cl): m/z=163 (M+H$^+$).

Preparation Two

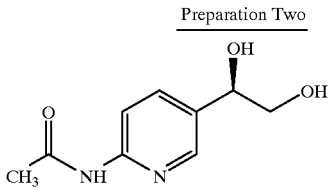

(R)-N-(5-(1,2-Dihydroxy-ethyl)-pyridin-2-yl)-acetamide.

A suspension of AD-Mix-B® (56.33 g) in water (200 ml) and t-butanol (200 ml) was cooled to 5° C. and N-(5-vinyl-pyridin-2-yl)-acetamide (prepared according to the procedure set forth in Preparation One, 6.52 g, 40.2 mmol) was added followed by 2-propanol (400 ml). The mixture was stirred at 5° C. for 12 hours and then at 20° C. for 12 hours. The reaction mixture was then treated with sodium sulfite (60.4 g), stirred for 30 minutes and then diluted with 500 ml of 2-propanol and stirred for an additional one hour. The mixture was filtered and the alcoholic phase was separated and evaporated to dryness. The residue was slurried in 500 ml of 2-propanol and evaporated again. The residue was dried to afford 6.35 g (80%) of the title product as colorless crystals. The crystals were recrystallized by dissolving in hot glacial acetic acid, diluting 7-fold with 2-propanol, cooling and seeding to give the title product as crystals. mp 184–185° C. $^1$H NMR (dmso-d$_6$): δ=8.22 (d, 1 H); 7.99 (d, 1 H); 7.68 (d of d, 1 H); 4.52 (t, 1 H); 3.44 (m, 2 H); 2.07 (s, 3 H). MS (Cl): m/z=197 (M+H$^+$). Optical Rotation: −4.52° (c=0.05, acetic acid). Analysis: Calculated for C$_9$H$_{12}$N$_2$O$_3$: C, 55.09%; H,6.17%; N, 14.28%. Found: C, 55.43%; H, 5.97%; N,13.96%.

Preparation Three

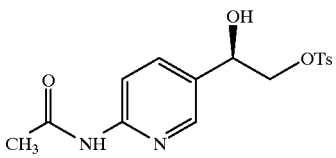

(R)-Toluene-4-sulfonic acid 2-(6-acetylamino-pyridin-3-yl)-2-hydroxy-ethyl Ester.

A slurry of (R)-N-(5-(1,2-dihydroxy-ethyl)-pyridin-2-yl)-acetamide (prepared according to the procedure set forth in Preparation Two, 71.2 g, 362 mmol) in anhydrous pyridine (362 ml) was cooled to 5° C. and treated with p-toluenesulfonyl chloride (69.18 g, 362 mmol) in one portion. The reaction mixture was stirred at 5° C. for 20 minutes, then the cooling bath was removed and the mixture was stirred at ambient temperature for two hours. The mixture was then concentrated, dissolved in 30 ml of methanol, concentrated and dissolved in toluene (300 ml) and concentrated again. The residue was treated again with methanol and toluene, then the residue was dissolved in ethyl acetate and washed sequentially with half-saturated brine with the addition of sodium carbonate, brine and dried over sodium sulfate. The filtrate was evaporated to afford 102.2 g (80%) of the title product as light buff crystals. Recrystallization from ethanol-cyclohexane afforded the title product as colorless crystals. mp 124–126° C. $^1$H NMR (dmso-d$_6$): δ=10.5 (br, 1 H); 8.21 (d, 1 H); 7.94 (d, 1 H); 7.68 (d, 2 H); 7.51 (d of d, 1 H); 7.41 (d, 1 H); 5.87 (d, 1 H); 4.76 (d of d, 1 H); 4.05 (d, 2 H); 2.41 (s, 3 H); 2.10 (s, 3 H). MS (Cl): m/z=351 (M+H$^+$). [a]$_D$−36.2 (c=1.19, acetone). Analysis: Calculated for C$_{16}$H$_{18}$N$_2$O$_5$S: C, 54.85%; H, 5.18%; N, 7.99%. Found: C, 54.91%; H, 5.34%; N, 8.06%.

Preparation Four

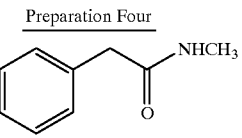

N-Methyl 4-hydroxyphenylacetamide.

Monomethylamine (22.43 kg, 722.15 mol, 6 eq.) was added over a 7-hour period to a solution of methyl-4-hydroxyphenylacetate (20.0 kg, 120.35 mol, 1.0 eq.) in methanol (120 L) and stirred overnight at room temperature. Methanol was then displaced under vacuum with ethyl acetate. The resulting slurry (about 75.7 L) was stirred at +10° C. for 1 hour, then filtered and dried under vacuum at 45° C. to yield of the title compound (18.68 kg, 94% of theory). mp 124–125° C. NMR (300 MHz, d$_6$-DMSO): δ=9.26 (s, 1H), 8.00–7.65 (br s, 1H), 7.21–6.90 (m, 2H), 6.86–6.55 (m, 2H), 3.26 (s, 2H), 2.75–2.45 (m, 3H).

Preparation Five

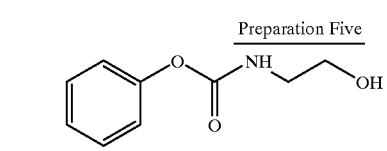

N-Benzyloxycarbonyl-2-aminoethanol.

Benzylchloroformate (44.95 kg, 263.5 mol, 1.0 eq.) was added over a 2 hour period at room temperature to a solution of ethanolamine (16.1 kg, 263.5 mol, 1.0 eq.) in water (129 L). After stirring for 30 minutes, this was added to a cold (5–10° C.) solution of NaHCO$_3$ (33.2 kg, 395.25 mol, 1.5 eq) in H$_2$O (330 L) over a 30 min period and then allowed to stir at room temperature overnight. Ethyl acetate (83 L) was added, the layers separated, and the aqueous layer extracted again with 83 L of ethyl acetate. The combined organic extracts were concentrated under vacuum to a volume of 38 L, and the remainder displaced with isopropyl ether. The resulting slurry was stirred and cooled to 10° C. for 2 hours, then filtered. The solids were washed with isopropyl ether and vacuum dried to give the title compound (39.1 kg, 71.1%). mp 61–63° C. NMR (300 MHz, d$_6$-DMSO): δ=7.50–7.37 (m, 5H), 7.37–7.16 (m, 1H), 5.05 (s, 2H), 4.70–4.63 (m, 1H), 3.46–3.37 (m, 2H), 3.13–3.03 (m, 2H).

Preparation Six

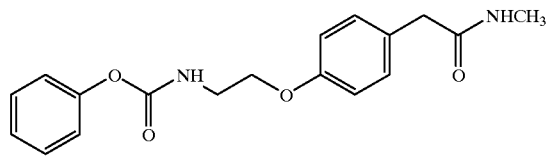

Methyl 4-(2-(N-benzyloxycarbonylamino)ethoxy) phenylacetamide.

The title compound of Preparation Four (18.68 kg, 113.14 mol. 1.0 eq.) and the title compound of Preparation Five (33.13 kg, 169.75 mol, 1.5 eq.) were dissolved in THF (151 L). Triphenylphosphine (44.5 kg, 169.75 mol, 1.5 eq.) was added and the mixture cooled to −5° C. Dilsopropyl azodicarboxylate (34.3 kg, 169.75 mol, 1.5 eq.) was added over an 8 hour period, and the reaction allowed to warm to room temperature overnight. Ethyl acetate (75 L) was added to the resulting white slurry, stirring was continued for 6 hours, and the solids filtered off and dried to yield crude title compound. (29.6 kg, 76.5% of theory, mp 131–133° C.). The crude product was slurried in ethyl acetate (148 L) for 3 hours at 10° C., then filtered, washed with 14 gal 10° C. ethyl acetate, and vacuum dried to yield the title compound (26.1 kg, 88.2 % recovery, 67.5% overall). mp 134–136° C. NMR (300 MHz, d$_6$-DMSO): δ=7.98–7.82 (m, 1H), 7.58–7.49 (m, 1H), 7.42–7.28 (m, 5H), 7.20–7.10 (d, 2H), 6.90–6.80 (d, 2H), 5.06 (s, 2H), 4.02–3.93 (m, 2H), 3.47–3.29 (m, 4H), 2.62–2.54 (d, 3H).

Preparation Seven

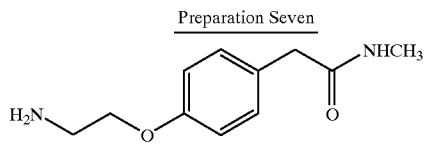

Methyl 4-(2-aminoethoxy)phenylacetamide.

The title compound of Preparation Six (18.4 kg, 53.73 mol) and 1.84 kg 10% palladium on carbon (50% H$_2$O wet) were suspended in 276 L of methanol under nitrogen, and the reaction vessel pressurized to 50 psig with hydrogen gas. This H$_2$ pressure was maintained by additional charges of H$_2$ until there was no further uptake of H$_2$ (approx. 20 hours) and the reaction was complete by thin layer chromatography. After purging the vessel with N$_2$, the mixture was heated to 45° C. and filtered at this temperature through Celite®. The solvent was displaced with toluene until a final volume of 30 L was achieved. After cooling to 5° C. the resulting solids were filtered off, washed with cold toluene, and vacuum dried to give the title compound (9.95 kg, 88.9% of theory). NMR (300 MHz, d$_6$-DMSO): δ=7.99–7.57 (m, 1H), 7.20–7.10 (d, 2H), 6.90–6.80 (d, 2H), 3.93–3.83 (m, 2H), 3.30 (s, 2H), 3.00–2.62 (m, 4H), 2.57 (d, 2H).

What is claimed is:

1. A compound of the Formula II,

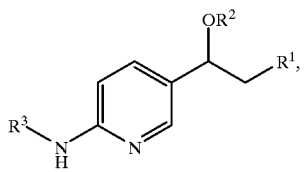

an enantiomer thereof or a pharmaceutically acceptable salt thereof, wherein:
  $R^1$ is a leaving group selected from halo, methanesulfonyloxy, benzenesulfonyloxy, p-toluenesulfonyloxy, m-nitrobenzenesulfonyloxy and p-nitrobenzenesulfonyloxy;
  $R^2$ is tetrahydrofuranyl, tetrahydropyranyl or a silyl protecting group; and
  $R^3$ is (C$_1$–C$_5$)alkanoyl or benzoyl optionally substituted independently with up to three (C$_1$–C$_4$)alkyl, (C$_1$–C$_4$) alkoxy or halo.

2. A compound of claim 1, an enantiomer thereof or a pharmaceutically acceptable salt thereof, wherein $R^2$ is SiR$^5$R$^6$R$^7$, wherein $R^5$, $R^6$ and $R^7$ are each independently (C$_1$–C$_4$)alkyl or aryl.

3. A compound of claim 2, an enantiomer thereof or a pharmaceutically acceptable salt thereof, wherein $R^3$ is acetyl, $R^1$ is toluenesulfonyloxy and said silyl protecting group is selected from t-butyldimethylsilyl, triethylsilyl and triisopropylsilyl.

4. The compound of claim 3, an enantiomer thereof or a pharmaceutically acceptable salt thereof, wherein $R^2$ is t-butyldimethylsilyl.

5. The compound of claim 4 or a pharmaceutically acceptable salt thereof having (R) stereochemistry.

6. The compound of claim 4 which is toluene-4-sulfonic acid 2-(6-acetylamino-pyridin-3-yl)-2(R)-(tert-butyl-dimethyl-silyloxy)-ethyl ester.

7. A process for preparing a compound of the Formula II,

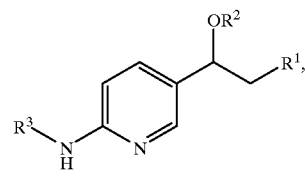

or an enantiomer thereof, wherein
  $R^1$ is a leaving group selected from halo, methanesulfonyloxy, p-toluenesulfonyloxy, benzenesulfonyloxy, m-nitrobenzenesulfonyloxy and p-nitrobenzenesulfonyloxy;
  $R^2$ is tetrahydrofuranyl, tetrahydropyranyl or a silyl protecting group; and
  $R^3$ is (C$_1$–C$_5$)alkanoyl or benzoyl optionally substituted independently with up to three (C$_1$–C$_4$)alkyl, (C$_1$–C$_4$) alkoxy or halo, comprising reacting a compound of the Formula IV,

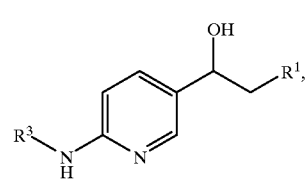

or an enantiomer thereof, wherein $R^1$ and $R^3$ are as defined above with a silylating agent and a suitable base in a reaction inert solvent for about 12 hours to about 18 hours at about 20° C. to about 50° C.

8. A process of claim 7 wherein said suitable base is imidazole.

9. A process of claim 8 wherein $R^1$ is p-toluenesulfonyloxy, $R^3$ is acetyl and said silylating agent is t-butyldimethylchlorosilane.

10. A process of claim 9 wherein

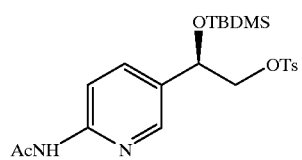

is prepared from

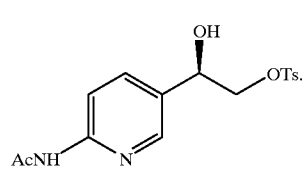

* * * * *